(12) United States Patent
Yamaguchi et al.

(10) Patent No.: US 7,700,800 B2
(45) Date of Patent: Apr. 20, 2010

(54) METHOD FOR PRODUCING FLUORINE-CONTAINING ALKYL (METH)ACRYLATE

(75) Inventors: Masao Yamaguchi, Ibaraki (JP); Fumihiko Yamaguchi, Osaka (JP)

(73) Assignees: Tokuyama Corporation, Shunan-Shi, Yamaguchi (JP); Daikin Industries Ltd., Kita-ku, Osaka-shi (JP)

( * ) Notice: Subject to any disclaimer, the term of this patent is extended or adjusted under 35 U.S.C. 154(b) by 12 days.

(21) Appl. No.: 11/908,720

(22) PCT Filed: Mar. 15, 2006

(86) PCT No.: PCT/JP2006/305632

§ 371 (c)(1),
(2), (4) Date: Sep. 14, 2007

(87) PCT Pub. No.: WO2006/098487

PCT Pub. Date: Sep. 21, 2006

(65) Prior Publication Data

US 2009/0023948 A1 Jan. 22, 2009

(30) Foreign Application Priority Data

Mar. 15, 2005 (JP) ............................. 2005-073577

(51) Int. Cl.
*C07C 69/52* (2006.01)
(52) U.S. Cl. ....................................................... 560/223
(58) Field of Classification Search ....................... None
See application file for complete search history.

(56) References Cited

U.S. PATENT DOCUMENTS

| 3,409,658 | A | * | 11/1968 | Emmons | 558/484 |
| 3,655,732 | A | * | 4/1972 | Scriver | 560/222 |
| 3,890,376 | A | | 6/1975 | Jager | |
| 4,859,793 | A | | 8/1989 | Hurtel | |

FOREIGN PATENT DOCUMENTS

| GB | 971732 | 10/1964 |
| JP | 49-75520 | 7/1974 |
| JP | 59-175452 | 10/1984 |
| JP | 59-181239 | 10/1984 |
| JP | 61-180743 | 8/1986 |
| JP | 62-063541 | 3/1987 |
| JP | 62-96451 | 5/1987 |
| JP | 02-295948 | 12/1990 |
| JP | 03-163044 | 7/1991 |
| JP | 05-345743 | 12/1993 |
| JP | 6-293705 A | 10/1994 |
| JP | 2002-187868 | 7/2002 |
| JP | 2004-250379 A | 9/2004 |

OTHER PUBLICATIONS

Solomons, Organic Chemistry, 5th Edition, 1992, John Wiley & Sons, Inc., pp. 86-90.*
A.I. Rakhimov et al.; Russian Journal of Applied Chemistry, 2002, vol. 75, No. 7, pp. 1162-1165. Cited in International Search Report.
Krupers, et al.; "Synthesis and Characterization of Semifluorinated Polymers Via Group Transfer Polymerization": Journal of Fluorine Chemistry; vol. 82, 1997, pp. 119-124.
Germain et al.; "Oxydation Anodique de Iodoperfluoroalcanes Dans Les Acides Perfluoroalcanesulfoniques. Preparation de Nouveaux Esters Sulfoniques Totalement Fluores . . . "; Tetrahedron, 1981, vol. 37, pp. 487-491.
Elshani, et al.; "Macrocyclic Ligands with Partially Fluorinated Sidearms: Synthesis and Metal ion Complexation"; Tetrahedron, 2000, vol. 56, pp. 3291-3301.

* cited by examiner

*Primary Examiner*—Paul A Zucker
(74) *Attorney, Agent, or Firm*—Norris, McLaughlin & Marcus

(57) ABSTRACT

The present invention discloses a method for producing a fluorine-containing alkyl (meth)acrylate represented by the following general formula (2):

$$Rf-(CH_2)_k-[-A-(CH_2)_l-]_m-OCOCR=CH_2 \quad (2)$$

(wherein R is a hydrogen atom or a methyl group), characterized by reacting
a fluorine-containing alcohol represented by the following general formula (1):

$$Rf-(CH_2)_k-[-A-(CH_2)_l-]_m-OH \quad (1)$$

(wherein Rf is a perfluoroalkyl group having 1 to 21 carbon atoms; A is S, SO or $SO_2$; k is 0, 1 or 2; l is 1, 2 or 3; m is 0 or 1; however, a case of k=0 and m=0 is excluded),
(meth)acrylic acid, and
a sulfonic acid halide
in the presence of a base containing at least one kind of tertiary amine.

5 Claims, No Drawings

METHOD FOR PRODUCING FLUORINE-CONTAINING ALKYL (METH)ACRYLATE

TECHNICAL FIELD

The present invention relates to a method for producing an acrylic acid ester or a (meth)acrylic acid ester [these compounds may be hereinafter described together as (meth)acrylic acid ester]. More particularly, the present invention relates to a method for producing a fluorine-containing alkyl (meth)acrylate having a particular chemical structure by reacting a fluorine-containing alcohol of particular chemical structure, (meth)acrylic acid and a sulfonic acid halide in the presence of a base containing at least a tertiary amine.

BACKGROUND ART

The following methods have been known for obtaining an ester compound by reacting a fluorine-containing alcohol represented by the following general formula (A):

$$F(CF_2CF_2)_n CH_2CH_2OH \qquad (A)$$

(wherein n is an integer of 1 to 10) and having a chemical structure in which a perfluoroalkyl group having even-numbered carbon atoms is bonded to the β-carbon atom of ethyl alcohol [this structure corresponds to a compound of the general formula (1) described in this Description wherein k is 2 and m is 0], with (meth)acrylic acid.

A method of subjecting the fluorine-containing alcohol and (meth)acrylic acid to dehydration in the presence of an acid catalyst (Patent Literatures 1 to 4 shown below).

A method of subjecting the fluorine-containing alcohol and a (meth)acrylic acid ester to ester interchange in the presence of an acid catalyst (Patent Literatures 1 to 3 shown below).

A method of subjecting the fluorine-containing alcohol and (meth)acrylic acid chloride to dehydrochlorination (Patent Literatures 1 to 3 shown below).

Also, there is known a method of reacting the fluorine-containing alcohol and methacrylic acid anhydride in the presence of dimethylaminopyridine (a catalyst) (Non-Patent Literature 1 shown below).

Meanwhile, there is known a method of converting, into a (meth)acrylic acid ester, a fluorine-containing alcohol having a particular chemical structure different from the chemical structure of the above-mentioned fluorine-containing alcohol (A) and represented by the following general formula (B):

$$C_n F_{2n+1} CH_2 OH \qquad (B)$$

(wherein n is an integer of 3 to 9 in Patent Literature 5 shown below and an integer of 2 to 20 in Patent Literature 6 shown below) [the particular chemical structure corresponds to a compound of the general formula (1) described in this Description wherein k is 1 and m is 0] (Patent Literatures 5 and 6 shown below).

In the Patent Literature 5, it is described that, in subjecting the fluorine-containing alcohol of the general formula (B) and (meth)acrylic acid to dehydration to produce their ester, no reaction proceeds even when the above-mentioned acid catalyst is used. That is, since fluorine atom exhibits its characteristic property, it is difficult to predict whether or not esterification proceeds in the esterification of a fluorine-containing alcohol containing a large number of fluorine atoms.

Incidentally, in the Patent Literature 5, the fluorine-containing alcohol represented by the general formula (B) is reacted with acrylic acid chloride in the presence of barium chloride to obtain a (meth)acrylic acid ester. Also, in the Patent Literature 6, the fluorine-containing alcohol represented by the general formula (B) is reacted with (meth)acrylic acid anhydride in the presence of an acid catalyst.

In literatures other than shown above, there are disclosed various techniques (Patent Literatures 7 to 17) of using fluorine-containing alcohols of different structures to obtain corresponding (meth)acrylic acid esters. However, as mentioned previously, since fluorine atom has its characteristic property, it has been difficult to predict whether or not the esterification of such a fluorine-containing alcohol proceeds smoothly.

(Meth)acrylic acid chloride, which is widely used in these conventional techniques, is an esterification agent of high reactivity. However, having high reactivity, this esterification agent is unstable and difficult to handle, and has a drawback of forming a dimer with the passage of time (Patent Literature 18).

The method of subjecting a fluorine-containing alcohol and (meth)acrylic acid to dehydration using an acid catalyst, to obtain an ester, uses inexpensive raw materials and is economical and accordingly is employed widely. However, when the dehydration using an acid catalyst is applied in conversion of the fluorine-containing alcohol having a chemical structure represented by the general formula (A), into its (meth)acrylic acid ester, it was found drawbacks that (meth)acrylic acid is required in excess and that there is formed, besides the intended ester compound, a considerable amount of an impurity represented by the following general formula (C):

$$F(CF_2CF_2)_n CH_2CH_2OCOCHRCH_2OCH_2CH_2 (CF_2CF_2)_n F \qquad (C)$$

(wherein R is a hydrogen atom or a methyl group; and n is an integer of 1 to 10). This impurity is considered to be formed by addition of the fluorine-containing alcohol to the double bond of the produced (meth)acrylic acid ester.

Similarly, there is widely employed the method of using a lower alkyl (meth)acrylate [e.g. methyl (meth)acrylate] and conducting ester interchange in the presence of an acid catalyst, because the method uses inexpensive raw materials and is economical. However, it was found drawbacks that, when the above ester interchange is conducted using a particular, fluorine-containing alcohol represented by the general formula (A), a considerable amount of an impurity represented by the general formula (C) is formed similarly to the above case.

Further, it was found drawbacks that, when esterification of fluorine-containing alcohol is conducted using (meth)acrylic acid anhydride in the presence of an acid catalyst described in the Patent Literatures 6 to 10, the above-mentioned addition product [general formula (C)] is formed (in the Patent Literatures 7 to 10, the by-produced trifluoroacetic acid is a strong acid of pKa=0.5).

There is no formation of the above-mentioned addition product when, as in the Non-Patent Literature 1, a fluorine-containing alcohol and methacrylic acid anhydride are reacted under a basic condition. However, it is necessary to produce or procure (meth)acrylic acid anhydride. Acrylic anhydride, in particular, has a strong tearing property; therefore, in its production or handling, there is required a facility in which consideration has been made for the above problem. Therefore, such a method is unsuitable as a method for industrial production.

Meanwhile, it is known that the fluorine-containing alcohol represented by the general formula (A) reacts with a sulfonic acid halide in the presence of a tertiary amine to form its sulfonic acid ester (Non-Patent Literature 2). It is also known that this sulfonic acid ester releases a sulfonic acid salt under a basic condition to give an olefin (Non-Patent Literature 3).

As described above, production of fluorine-containing alkyl (meth)acrylate employs a highly characteristic reaction and, therefore, it is quite unpredictable whether or not the reaction proceeds smoothly.

Non-Patent Literature 1 Kruper, Maarten J.; Moeller Martin; J. Fluorine Chem., 1997, 82(2), 119-124.

Non-Patent Literature 2 Elshani, Sadik; Kobzar, Evgeny; Bartsh, Richard A.; Tetrahedron 2000, 56(21), 3291-3302

Non-Patent Literature 3 Germain, A.; Commeyras, A.; Tetrahedron 1981, 37, 487-492

Patent Literature 1 GB 971,732 (Page 3, Lines 10 to 16)
Patent Literature 2 U.S. Pat. No. 3,378,609 (Column 2, Line 71 to Column 3, Line 12)
Patent Literature 3 U.S. Pat. No. 3,547,856 (Column 2, Lines 47 to 59)
Patent Literature 4 JP-A-1986-180743 (Claims)
Patent Literature 5 U.S. Pat. No. 2,642,416 (Column 6, Lines 45 to 58)
Patent Literature 6 JP-A-1987-096451 (Claims)
Patent Literature 7 U.S. Pat. No. 3,177,185 (Column 2, Line 12 to Column 3, Line 9)
Patent Literature 8 U.S. Pat. No. 3,384,627 (Column 5, Lines 1 to 19)
Patent Literature 9 U.S. Pat. No. 3,438,946 (Column 2, Lines 3 to 9)
Patent Literature 10 U.S. Pat. No. 3,547,861 (Column 4, Lines 1 to 25)
Patent Literature 11 JP-A-1974-075520 (Claims)
Patent Literature 12 JP-A-1984-175452 (Claims)
Patent Literature 13 JP-A-1984-181239 (Claims)
Patent Literature 14 JP-A-1987-063541 (Claim 7)
Patent Literature 15 JP-A-1990-295948 (Claims)
Patent Literature 16 JP-A-1991-163044 (Claims)
Patent Literature 17 JP-A-1993-345743 (Claim 7)
Patent Literature 18 JP-A-2002-187868 [Paragraph (0002)]

DISCLOSURE OF THE INVENTION

The present inventor made a study on the esterification of a fluorine-containing alcohol specified by the general formula (1) (described later) into its (meth)acrylic acid ester. As a result, it was found that, when the above fluorine-containing alcohol, (meth)acrylic acid and a sulfonic acid halide are reacted in the presence of a base containing at least one kind of tertiary amine, substantially only intended esterification can be allowed to proceed (1) without substantial formation of any addition product [e.g. an impurity of the general formula (C)] and (2) without formation of a sulfonic acid ester of a fluorine-containing alcohol, or its corresponding, fluorine-containing olefin. The finding has led to the completion of the present invention.

Hence, the object of the present invention is to provide a method for efficiently producing a fluorine-containing alkyl (meth)acrylate represented by the general formula (2) by esterification of a fluorine-containing alcohol having a particular chemical structure, represented by the general formula (1), into its (meth)acrylic acid ester, which method can prevent the formation of an addition product such as represented by the general formula (C) and does not use any raw material such as (meth)acrylic acid chloride, which is unstable, changes strikingly with the passage of time and is difficult to handle.

The present invention is as described below.

[1] A method for producing a fluorine-containing alkyl (meth)acrylate represented by the following general formula (2):

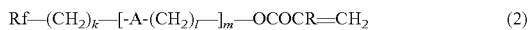

$$Rf-(CH_2)_k-[-A-(CH_2)_l-]_m-OCOCR=CH_2 \qquad (2)$$

(wherein R is a hydrogen atom or a methyl group; Rf is a perfluoroalkyl group having 1 to 21 carbon atoms; A is S, SO or $SO_2$; k is 0, 1 or 2; l is 1, 2 or 3; m is 0 or 1; however, a case of k=0 and m=0 is excluded), characterized by reacting
a fluorine-containing alcohol represented by the following general formula (1):

$$Rf-(CH_2)_k-[-A-(CH_2)_l-]_m-OH \qquad (1)$$

(wherein Rf is a perfluoroalkyl group having 1 to 21 carbon atoms; A is S, SO or $SO_2$; k is 0, 1 or 2; l is 1, 2 or 3; m is 0 or 1; however, a case of k=0 and m=0 is excluded),
(meth)acrylic acid, and
a sulfonic acid halide in the presence of a base containing at least one kind of tertiary amine.

[2] A method for producing a fluorine-containing alkyl (meth)acrylate, according to [1], wherein, in the general formula (1) and the general formula (2), Rf is a perfluoroalkyl group having 1 to 6 carbon atoms.

[3] A method for producing a fluorine-containing alkyl (meth)acrylate, according to [1], wherein, in the general formula (1) and the general formula (2), Rf is a perfluoroalkyl group represented by the following general formula (3):

$$F(CF_2CF_2)_n- \qquad (3)$$

(wherein n is an integer of 1 to 10).

[4] A method for producing a fluorine-containing alkyl (meth)acrylate, according to [1], wherein, in the general formula (1) and the general formula (2), k is 2 and m is 0.

[5] A method for producing a fluorine-containing alkyl (meth)acrylate, according to [1], wherein the sulfonic acid halide is a sulfonic acid halide represented by the following general formula (4):

$$R'SO_2X \qquad (4)$$

(wherein R' is a hydrocarbon group of 1 to 10 carbon atoms which may be substituted with halogen; and X is a halogen atom).

[6] A method for producing a fluorine-containing alkyl (meth)acrylate, according to any one of [1] to [3], wherein the base containing at least one kind of tertiary amine is a mixed base of a tertiary amine and an inorganic base.

In the present invention, in esterification reaction of a fluorine-containing alcohol specified by the general formula (1) into its (meth)acrylic acid ester, the fluorine-containing alcohol, (meth)acrylic acid and a sulfonic acid halide are reacted in the presence of a base containing at least one kind of tertiary amine. As a result, intended esterification can be allowed to proceed without substantial formation of an addition product [e.g. a compound represented by the general formula (C)] and further without formation of a sulfonic acid ester of fluorine-containing alcohol or its corresponding, fluorine-containing olefin. In this case, the selectivity and yield of an intended compound are extremely high. The tertiary amine may be used alone but combination use of the tertiary amine and an inorganic base can give the intended compound at a lower cost.

The fluorine-containing (meth)acrylic acid ester produced by the method of the present invention, when subjected to homopolymerization or copolymerization with other monomer, can give a polymer having water-repellency, lubricity, flame-retardancy, etc.

Therefore, the fluorine-containing (meth)acrylic acid ester produced by the method of the present invention is important as a functional monomer.

BEST MODE FOR CARRYING OUT THE INVENTION

The present invention is described in detail below.

(Fluorine-Containing Alcohol)

The fluorine-containing alcohol of particular chemical structure, used in the present invention is a compound represented by the following general formula (1):

$$Rf-(CH_2)_k-[-A-(CH_2)_l-]_m-OH \quad (1)$$

In the above formula, Rf is a perfluoroalkyl group having 1 to 21 carbon atoms; A is S, SO or $SO_2$; k is 0, 1 or 2; l is 1, 2 or 3; and m is 0 or 1. However, a case of k=0 and m=0 is excluded.

In the above formula, Rf is a perfluoroalkyl group having 1 to 21 carbon atoms, preferably a perfluoroalkyl group having 1 to 6 carbon atoms, particularly preferably a perfluoroalkyl group having 1 to 4 carbon atoms.

As Rf, there can be mentioned perfluoroalkyl groups represented by the following formula (3):

$$F(CF_2CF_2)_n- \quad (3)$$

(wherein n is an integer of 1 to 10).

Of the perfluoroalkyl groups represented by the above formula (3), there are preferred those in which n is 1 to 3. As specific examples of these perfluoroalkyl groups, there can be mentioned $CF_3CF_2-$, $CF_3CF_2CF_2CF_2-$ and $CF_3CF_2CF_2CF_2CF_2CF_2-$.

As the perfluoroalkyl groups other than represented by the above formula (3), there can be mentioned $CF_3-$, $CF_3CF_2CF_2-$, $(CF_3)_2CF-$, $(CF_3)_2CFCF_2-$, $(CF_3)_3C-$, $CF_3(CF_2)_4-$, $(CF_3)_2CF(CF_2)_2-$, $(CF_3)_3CCF_2-$, $CF_3CF_2CF_2CF(CF_3)-$, $CF_3(CF_2)_5-$, $(CF_3)_2CF(CF_2)_3-$, $(CF_3)_2CF(CF_2)_4-$, $CF_3(CF_2)_7-$, $(CF_3)_2CF(CF_2)_5-$, $(CF_3)_2CF(CF_2)_6-$, $CF_3(CF_2)_9-$, etc.

In the general formula (1), k is 0, 1 or 2, preferably 2 or 3; and l is 1, 2 or 3, preferably 2 or 3.

Examples of the fluorine-containing alcohol represented by the general formula (1) include the following compounds.

Rf—$(CH_2)_2$—OH

Rf—S—$(CH_2)_2$—OH

Rf—S—$(CH_2)_3$—OH

Rf—$(CH_2)_2$—S—$(CH_2)_2$—OH

Rf—SO—$(CH_2)_2$—OH

Rf—SO—$(CH_2)_3$—OH

Rf—$(CH_2)_2$—SO—$(CH_2)_2$—OH

Rf—$SO_2$—$(CH_2)_2$—OH

Rf—$SO_2$—$(CH_2)_3$—OH

Rf—$(CH_2)_2$—$SO_2$—$(CH_2)_2$—OH

The fluorine-containing alcohol having the above structure can be produced by the following methods.

For example, a fluorine-containing alcohol of the general formula (1) wherein k is 2 and m is 0, can be produced by converting a perfluoroalkyl iodide [which corresponds to a fluorine-containing alcohol of the general formula (1)] into its nitric acid ester and then hydrolyzing this nitric acid ester, as described in Patent Literature DE 2028459.

Also, for example, a fluorine-containing alcohol of the general formula (1) wherein k is 0, l is 2 and m is 1, can be produced as follows. That is, a perfluoroalkyl iodide [which corresponds to a fluorine-containing alcohol of the general formula (1)] and mercaptoethanol are reacted in a solvent (for example, water/N,N-dimethylformamide), for example, at 30 to 90° C. for 0.5 to 30 hours, whereby a perfluoroalkylthioethanol can be obtained. Then, acetic acid solution of the perfluoroalkylthioethanol obtained is added aqueous hydrogen peroxide, and they are reacted, for example, at 30 to 80° C. for 0.5 to 10 hours. Thereafter, the partially produced acetic acid ester is hydrolyzed, whereby a perfluoroalkylsulfinylethanol or a perfluoroalkylsulfonylethanol can be produced depending upon the oxidation degree caused by the aqueous hydrogen peroxide.

The perfluoroalkyl iodide can be obtained, as described in, for example, Patent Literature NL 6506069, by heating, at 330° C. for 45 seconds, ethylene and an iodinated perfluoroalkane having the same carbon skeleton as the perfluoroalkyl group of the fluorine-containing alcohol represented by the general formula (1). Or, the perfluoroalkyl iodide can be obtained, as described in Patent Literature U.S. Pat. No. 4,058,573, by heating a corresponding iodinated perfluoroalkane and ethylene together with a radical-generating agent such as isobutyl peroxide or the like.

The corresponding perfluoroalkyl iodide can also be obtained by other various methods described in Patent Literature U.S. Pat. No. 3,083,238, FR 1385682, GB 868494, U.S. Pat. No. 3,083,224, etc.

(Sulfonic Acid Halide)

In the present invention, a sulfonic acid halide is used. There is no particular restriction as to the sulfonic acid halide; however, a compound represented by the following general formula (4) is preferred:

$$R'SO_2X \quad (4)$$

(wherein R' is a hydrocarbon group having 1 to 10 carbon atoms, which may be substituted with halogen, and X is a halogen atom).

As R', there can be mentioned alkyl groups such as methyl group, ethyl group, propyl group, butyl group and the like; aromatic hydrocarbon groups such as phenyl group, toluoyl group and the like; and groups wherein the above groups are substituted with halogen atom such as fluorine atom, chlorine atom, bromine atom or the like. When the hydrocarbon group is an alkyl group substituted with halogen atom, the halogen atom is preferred to be fluorine atom, in particular.

When R' is an alkyl group, the carbon atoms thereof are preferably 1 to 8. When the alkyl group is substituted with fluorine atom, it is preferred that all the hydrogen atoms of alkyl group is replaced by fluorine atoms, that is, the alkyl group is a perfluoroalkyl group. Also, when R' is an aromatic hydrocarbon group, the group is preferably phenyl group or toluoyl group. When R' is an aromatic hydrocarbon group substituted with halogen atom, the aromatic hydrocarbon group is preferably phenyl group, specifically fluorophenyl group, chlorophenyl group, bromophenyl group, perfluorophenyl group or the like.

X is a halogen atom such as fluorine atom, chlorine atom, bromine atom, iodine atom or the like. Of these halogen atoms, chlorine atom is preferred from the availability. From the industrial availability, there are preferred methanesulfonic acid chloride, benzenesulfonic acid chloride and toluenesulfonic acid chloride. From the good reactivity, there are preferred trifluoromethanesulfonic acid chloride, perfluorobutanesulfonic acid chloride, perfluorooctanesulfonic acid chloride and bromobenzenesulfonic acid chloride.

The use amount of the sulfonic acid halide is normally 1 mole relative to 1 mole of the fluorine-containing alcohol represented by the general formula (1). An excessive amount of the sulfonic acid halide may be used in order to increase the conversion of the fluorine-containing alcohol. Too excessive an amount of the sulfonic acid halide relative to the fluorine-containing alcohol is uneconomical. Ordinarily, the amount of the sulfonic acid halide is preferably 1 to 3 moles, more preferably 1.5 to 2 moles relative to 1 mole of the fluorine-containing alcohol.

(Base)

In the production method of the present invention, the reaction is conducted in the presence of a base containing at least one kind of tertiary amine. The total amount of the base may be a tertiary amine.

There is no particular restriction as to the tertiary amine used. As the tertiary amine, there can be used a cyclic or acyclic aliphatic tertiary amine, an aromatic tertiary amine, a non-aromatic unsaturated tertiary amine, a heterocyclic tertiary amine, or a combination thereof.

As the cyclic aliphatic tertiary amine, there can be mentioned N-alkylpyrrolidine, N-alkylpiperidine, N-alkylmorpholine, N,N'-dialkylpiperazine, quinuclidine, 1,4-diazabicyclo[2.2.2]octane (DABCO), etc.

As the acyclic aliphatic tertiary amine, there can be mentioned trialkylamine, benzyldialkylamine, dibenzylalkylamine, dialkylphenethylamine, etc.

As the aromatic tertiary amine, there can be mentioned N,N-dialkylaniline, diphenylalkylamine, etc.

As the non-aromatic unsaturated tertiary amine, there can be mentioned 1,5-azabicyclo[4.3.0]non-5-ene (DBN), 1,8-diazabicyclo[5.4.0]undec-7-ene (DBU), etc.

As the heterocyclic tertiary amine, there can be mentioned pyridine, 4-dimethylaminopyridine (DMAP), pyrimidine, N-alkylimidazole, quinoline, etc.

Of these, triethylamine, N-methylmorpholine and pyridine are preferred for their industrial availability, handleability, etc.; and DABCO, DBN, DBU and DMAP are preferred for their high reactivity. It is also preferred to use a tertiary amine of high reactivity in a catalytic amount, in combination with an amine of good availability.

The use amount of the base is preferred to be ordinarily 2 to 6 moles relative to 1 mole of the fluorine-containing alcohol. Use of the base in an excessive amount is uneconomical. When only a tertiary amine is used as the base, the amount is normally 2 moles relative to 1 mole of the fluorine-containing alcohol of the general formula (1); however, the tertiary amine may be used in excess in order to increase the conversion of the fluorine-containing alcohol.

It is possible to use, as the base, a tertiary amine in a catalytic amount, in combination with an inorganic base. As the inorganic base, there can be mentioned, for example, sodium carbonate, sodium hydrogencarbonate and potassium carbonate. In this case, it is preferred that the amount of the tertiary amine is 0.01 to 0.5 mole and the amount of the inorganic base used in combination is 1.5 to 6 moles, both relative to 1 mole of the fluorine-containing alcohol.

[(Meth)acrylic Acid]

In the present invention, the use amount of (meth)acrylic acid is normally 1 mole relative to 1 mole of the fluorine-containing alcohol represented by the general formula (1). However, (meth)acrylic acid may be used in excess in order to increase the conversion of the fluorine-containing alcohol. Use of (meth)acrylic acid in large excess is uneconomical. Therefore, it is desired that (meth)acrylic acid is used ordinarily in an amount of 1 to 3 moles, preferably 1.5 to 2 moles relative to 1 mole of the fluorine-containing alcohol.

The reaction of the present invention may be conducted in the presence of a solvent. As to the solvent, there is no particular restriction as long as it does not hinder the reaction. Specifically, there can be mentioned, as the solvent, hydrocarbons, chlorinated hydrocarbons, ethers, aprotic polar solvents, etc.

As the hydrocarbons, there can be mentioned aliphatic hydrocarbons such as hexane, heptane and the like, and aromatic hydrocarbons such as toluene, xylene and the like.

As the chlorinated hydrocarbons, there can be mentioned methylene chloride, chloroform, ethylene dichloride, trichloroethylene, etc.

As the ethers, there can be mentioned diethyl ether, diisopropyl ether, tetrahydrofuran, dioxane, etc.

As the aprotic polar solvents, there can be mentioned dimethylformamide, N-methylpyrrolidinone, dimethyl sulfoxide, sulfolane, hexamethylphosphoric triamide, etc.

The biggest feature of the present invention lies in that a reaction is conducted in the presence of a fluorine-containing alcohol of particular chemical structure, represented by the general formula (1), (meth)acrylic acid, a sulfonic acid halide and a tertiary amine. As to the addition order of individual raw material compounds, there is no particular restriction; however, there is preferred an order in which the fluorine-containing alcohol, (meth)acrylic acid and the sulfonic acid halide are dissolved in a solvent and the tertiary amine is added lastly, or an order in which the fluorine-containing alcohol, (meth)acrylic acid and the tertiary amine are dissolved in a solvent and the sulfonic acid halide is added lastly. When the individual compounds are added in this order, it is easy to control the reaction heat generated with the progress of reaction.

The reaction temperature is not particularly restricted as long as it is not an extremely low temperature or an extremely high temperature. The reaction temperature is preferably 0° C. to a temperature not higher than the boiling point of the solvent and is ordinarily 100° C. or lower. Since the reaction is exothermic, the reaction is preferably conducted while the reaction mixture is cooled. The reaction time differs greatly depending upon the reaction temperature, the efficiency of cooling, etc. Ordinarily, the reaction is substantially over when all the raw materials have been added. After the addition, an aging time of about 1 to 24 hours may be taken.

EXAMPLES

The present invention is described specifically below by way of Examples. However, the present invention is in no way restricted to these Examples. In the Examples, conversion and selectivity have the following definitions.

Conversion(%)=100−100×$A/(A+B+C)$

Selectivity of ester(%)=100×$B/(B+C)$

In the above, A is a peak area of a fluorine-containing alcohol, recorded in a record paper in gas chromatography; B is a peak area of a fluorine-containing alkyl (meth)acrylate, recorded in the same paper; and C is a peak area of an impurity [an addition product formed by addition of a fluorine-containing alcohol to a fluorine-containing alkyl (meth)acrylate], recorded in the same paper.

Example 1

In a 3-liter, four-necked glass reactor were placed 1 liter of methylene chloride, 100 g (379 mmol) of 3,3,4,4,5,5,6,6,6-nonafluorohexanol, 30 g (417 mmol) of acrylic acid, 73 g (414 mmol) of benzenesulfonic acid chloride and 0.5 g of a polymerization inhibitor (Sumilizer GM, a product of Sumitomo Chemical Co., Ltd.). At this point, the mixture caused substantially no heat generation.

Then, while the mixture was cooled at 40° C. or lower, 84 g (832 mmol) of triethylamine was slowly added dropwise. After the completion of the dropwise addition, the mixture was stirred at 30° C. for 3 hours. The reaction mixture obtained was subjected to gas chromatography for analysis. The conversion was 99% or more and the selectivity was 99%. 250 ml of water was added to the reaction mixture, followed by stirring for 30 minutes. The mixture was allowed to stand. An organic layer separated was divided. The organic layer was washed two times each with 250 ml of water, after which the organic layer was subjected to distillation under reduced pressure to remove the methylene chloride contained therein.

To the distillation residue obtained was added 0.5 g of a polymerization inhibitor, Sumilizer GM. The mixture was subjected to distillation under reduced pressure to obtain 92 g (289 mmol, yield: 76%) of 3,3,4,4,5,5,6,6,6-nonafluorohexyl acrylate.

Example 2

In a 5-liter, four-necked glass reactor were placed 3 liters of methylene chloride, 7 g (69 mmol) of triethylamine, 81 g (764 mmol) of sodium carbonate, 100 g (379 mmol) of 3,3,4,4,5,5,6,6,6-nonafluorohexanol and 0.5 g of Sumilizer GM. Thereto was dropwise added 55 g (764 mmol) of acrylic acid. Then, 135 g (765 mmol) of benzenesulfonic acid chloride was added dropwise while the reaction temperature was kept at 40° C. or lower. After the completion of the dropwise addition, stirring was conducted at 30° C. for 2 hours to obtain a reaction mixture. At this point, the conversion was 88% and the selectivity was 99%.

400 ml of water was added to the reaction mixture. Stirring was conducted for 1 hour. Then, the reaction mixture was allowed to stand. An organic layer was separated from an aqueous layer. The organic layer was subjected to distillation under reduced pressure to remove methylene chloride. To the distillation residue obtained was added 2 liters of methylene chloride. There were further added 15 g (148 mmol) of triethylamine and 10 g (139 mmol) of acrylic acid. To the mixture was dropwise added 24 g (136 mmol) of benzenesulfonic acid chloride while the reaction temperature was kept at 40° C. or lower. After the completion of the dropwise addition, stirring was conducted for 2 hours while the temperature of reaction mixture was kept at 30° C. At this point, the conversion was 99% or more and the selectivity was 99%.

250 ml of water was added to the reaction mixture, followed by stirring for 30 minutes. The reaction mixture was allowed to stand. An organic layer was separated from an aqueous layer. The organic layer was washed two times each with 250 ml of water, after which the organic layer was subjected to distillation under reduced pressure to remove the methylene chloride contained therein. To the distillation residue obtained was added 0.5 g of a polymerization inhibitor, Sumilizer GM. The mixture was subjected to distillation under reduced pressure to obtain 101 g (317 mmol, yield: 84%) of 3,3,4,4,5,5,6,6,6-nonafluorohexyl acrylate.

Example 3

In a 200-ml, three-necked glass reactor were placed 80 ml of methylene chloride, 10 g (38 mmol) of 3,3,4,4,5,5,6,6,6-nonafluorohexanol, 5 g (58 mmol) of methacrylic acid, 10 g (57 mmol) of benzenesulfonic acid chloride and 0.1 g of a polymerization inhibitor, Sumilizer GM. While the reaction temperature was kept at 40° C. or lower, 12 g (119 mmol) of triethylamine was added dropwise. After the completion of the dropwise addition, stirring was conducted at room temperature for 1 hour. At this point, the conversion was 99% and the selectivity was 99%.

Example 4

In a 200-ml, three-necked glass reactor were placed 80 ml of tetrahydrofuran, 10 g (27.5 mmol) of 3,3,4,4,5,5,6,6,7,7,8,8,8-tridecafluorooctanol, 5 g (69 mmol) of acrylic acid, 10 g (57 mmol) of benzenesulfonic acid chloride and 0.1 g of a polymerization inhibitor, Sumilizer GM and allow to solve them. While the reaction temperature was kept at 40° C. or lower, 12 g (119 mmol) of triethylamine was added dropwise. After the completion of the dropwise addition, stirring was conducted at room temperature for 1 hour. At this point, the conversion was 99% and the selectivity was 99%.

Example 5

In a 200-ml, three-necked glass reactor were placed 80 ml of toluene, 10 g (38 mmol) of 3,3,4,4,5,5,6,6,6-nonafluorohexanol, 5 g (69 mmol) of acrylic acid, 7 g (61 mmol) of methanesulfonic acid chloride and 0.1 g of a polymerization inhibitor, Sumilizer GM. While the reaction temperature was kept at 40° C. or lower, 15 g (149 mmol) of triethylamine was added dropwise. After the completion of the dropwise addition, stirring was conducted at room temperature for 1 hour. At this point, the conversion was 98% and the selectivity was 99%.

Comparative Example 1

In a 100-ml, three-necked glass reactor were placed 50 ml of methylene chloride, 10 g (38 mmol) of 3,3,4,4,5,5,6,6,6-nonafluorohexanol, 10 g (139 mmol) of acrylic acid, 0.1 g of a polymerization inhibitor, Sumilizer GM and 0.2 of toluenesulfonic acid. The mixture was heated. A reaction was allowed to proceed while distillation was made under normal pressure to remove the generated water together with methylene chloride. Every time when the amount of methylene chloride became small and the reactor-inside temperature exceeded 43° C., fresh methylene chloride was added into the reactor, to conduct the reaction for total 10 hours. At this point, the conversion was 82% and the selectivity was 84%.

Example 6

In a 100-ml, three-necked glass reactor were placed 50 ml of methylene chloride, 10 g (38 mmol) of 3,3,4,4,5,5,6,6,6-nonafluorohexanol, 5 g (69 mmol) of acrylic acid, 7 g (40 mmol) of benzenesulfonic acid chloride and 0.1 g of a polymerization inhibitor, Sumilizer GM. While the reactor-inside temperature was kept at 40° C. or lower, 14 g (139 mmol) of N-methylmorpholine was added dropwise. At this point, the conversion was 95% and the selectivity was 99%.

Example 7

In a 200-ml, three-necked glass reactor were placed 80 ml of methylene chloride, 13.0 g (38.0 mmol) of 3-(perfluorobutylsulfonyl)propan-1-ol, 3.83 g (53.2 mmol) of acrylic acid, 9.30 g (52.7 mmol) of benzenesulfonic acid chloride and 0.1 g of a polymerization inhibitor, Sumilizer GM. The mixture was cooled in an ice bath and stirred. Then, while the reaction temperature was kept at 10° C. or lower, 11.5 g (114 mmol) of triethylamine was added dropwise. After the completion of the dropwise addition, stirring was conducted at room temperature for 1 hour. At this point, the conversion was 99% and the selectivity was 99%.

Example 8

In a 200-ml, three-necked glass reactor were placed 80 ml of methylene chloride, 11.8 g (38.0 mmol) of 3-(perfluorobutylsulfinyl)propan-1-ol, 3.83 g (53.2 mmol) of acrylic acid, 9.30 g (52.7 mmol) of benzenesulfonic acid chloride and 0.1 g of a polymerization inhibitor, Sumilizer GM. The mixture was stirred while being cooled in an ice bath. Then, while the reaction temperature was kept at 10° C. or lower, 11.5 g (114 mmol) of triethylamine was added dropwise. After the completion of the dropwise addition, stirring was conducted at room temperature for 1 hour. At this point, the conversion was 99% and the selectivity was 99%.

Example 9

In a 200-ml, three-necked glass reactor were placed 80 ml of methylene chloride, 13.5 g (38.0 mmol) of 3-(perfluorobutylethylsulfonyl)propan-1-ol, 3.83 g (53.2 mmol) of acrylic acid, 9.30 g (52.7 mmol) of benzenesulfonic acid chloride and 0.1 g of a polymerization inhibitor, Sumilizer GM. The mixture was stirred while being cooled in an ice bath. Then, while the system temperature was kept at 10° C. or lower, 11.5 g (114 mmol) of triethylamine was added dropwise. After the completion of the dropwise addition, stirring was conducted at room temperature for 1 hour. At this point, the conversion was 99% and the selectivity was 99%.

Comparative Example 2

In a 100-ml, three-necked glass reactor were placed 50 ml of cyclohexane, 13.0 g (38.0 mmol) of 3-(perfluorobutylsulfonyl)propan-1-ol, 3.83 g (53.2 mmol) of acrylic acid, 0.2 g of toluenesulfonic acid and 0.1 g of a polymerization inhibitor, Sumilizer GM. The mixture was stirred with heating. A reaction was allowed to proceed while distillation was made under normal pressure to remove the water generated during the reaction, together with cyclohexane. The reaction was conducted for total 16 hours at a reactor-inside temperature of 80 to 85° C. At this point, the conversion was 85% and the selectivity was 80%. The reaction product was analyzed. As a result, there was confirmed presence of 15% of a compound (a by-product) formed by addition of 3-(perfluorobutylsulfonyl)propan-1-ol to the double bond of an intended acrylic acid ester.

Comparative Example 3

In a 50-ml, three-necked glass reactor were placed 26.0 g (76.0 mmol) of 3-(perfluorobutylsulfonyl)propan-1-ol, 9.16 g (106.4 mmol) of methyl acrylate, 0.2 g of sulfuric acid and 0.2 g of a polymerization inhibitor, Sumilizer GM. The mixture was stirred with heating. A reaction was allowed to proceed while distillation was made under normal pressure to remove the methanol generated. The reactor-inside temperature was 70 to 75° C. and the reaction was conducted for total 16 hours. At this point, the conversion was 83% and the selectivity was 86%. The reaction product was analyzed. As a result, there was confirmed presence of 12% of a compound (a by-product) formed by addition of 3-(perfluorobutylsulfonyl)propan-1-ol to the double bond of an intended acrylic acid ester.

Comparative Example 4

In a 50-ml, three-necked glass reactor were placed 26.0 g (76.0 mmol) of 3-(perfluorobutylsulfonyl)propan-1-ol, 12.7 g (92.0 mmol) of acrylic acid, 0.2 g of sulfuric acid and 0.2 g of a polymerization inhibitor, Sumilizer GM. A reaction was conducted for total 5 hours with the reactor-inside temperature kept at 65 to 70° C. At this point, the conversion was 89% and the selectivity was 84%. The reaction product was analyzed. As a result, there was confirmed presence of 12% of a compound (a by-product) formed by addition of 3-(perfluorobutylsulfonyl)propan-1-ol to the double bond of an intended acrylic acid ester.

The invention claimed is:

1. A method for producing a fluorine-containing alkyl (meth)acrylate represented by the following general formula (2):

$$Rf-(CH_2)_k-[-A-(CH_2)_l-]_m-OCOCR=CH_2 \qquad (2)$$

(wherein R is a hydrogen atom or a methyl group; Rf is a perfluoroalkyl group having 1 to 21 carbon atoms; A is S, SO or $SO_2$; k is 0, 1 or 2; l is 1, 2 or 3; m is 0 or 1; however, a case of k=0 and m=0 is excluded), characterized by reacting a fluorine-containing alcohol represented by the following general formula (1):

$$Rf-(CH_2)_k-[-A-(CH_2)_l-]_m-OH \qquad (1)$$

(wherein Rf is a perfluoroalkyl group having 1 to 21 carbon atoms; A is S, SO or $SO_2$; k is 0, 1 or 2; l is 1, 2 or 3; m is 0 or 1; however, a case of k=0 and m=0 is excluded), (meth)acrylic acid, and a sulfonic acid halide in the presence of a mixed base of a tertiary amine and an inorganic base selected from the group consisting of sodium carbonate, sodium hydrogencarbonate and potassium carbonate.

2. A method for producing a fluorine-containing alkyl (meth)acrylate, according to claim 1, wherein, in the general formula (1) and the general formula (2), Rf is a perfluoroalkyl group having 1 to 6 carbon atoms.

3. A method for producing a fluorine-containing alkyl (meth)acrylate, according to claim 1, wherein, in the general formula (1) and the general formula (2), Rf is a perfluoroalkyl group represented by the following general formula (3):

$$F(CF_2CF_2)_n- \qquad (3)$$

(wherein n is an integer of 1 to 10).

4. A method for producing a fluorine-containing alkyl (meth)acrylate, according to claim 1, wherein, in the general formula (1) and the general formula (2), k is 2 and m is 0.

5. A method for producing a fluorine-containing alkyl (meth)acrylate, according to claim 1, wherein the sulfonic acid halide is a sulfonic acid halide represented by the following general formula (4):

$$R'SO_2X \qquad (4)$$

(wherein R' is a hydrocarbon group of 1 to 10 carbon atoms which may be substituted with halogen; and X is a halogen atom).

* * * * *